(12) United States Patent
Nishijima et al.

(10) Patent No.: US 11,215,558 B2
(45) Date of Patent: Jan. 4, 2022

(54) NANOSTRUCTURE ARRAY, HYDROGEN DETECTION ELEMENT, AND HYDROGEN DETECTION DEVICE

(71) Applicants: National University Corporation YOKOHAMA National University, Kanagawa (JP); TOKYO OHKA KOGYO CO., LTD., Kanagawa (JP)

(72) Inventors: Yoshiaki Nishijima, Yokohama (JP); Shinji Okazaki, Yokohama (JP); Takaaki Beni, Ebina (JP); Naoki Yamasaku, Kawasaki (JP); Takeshi Iwai, Kawasaki (JP)

(73) Assignees: NATIONAL UNIVERSITY CORPORATION YOKOHAMA NATIONAL UNIVERSITY, Kanagawa (JP); TOKYO OHKA KOGYO CO., LTD., Kanagawa (JP)

( * ) Notice: Subject to any disclaimer, the term of this patent is extended or adjusted under 35 U.S.C. 154(b) by 0 days.

(21) Appl. No.: 16/793,728

(22) Filed: Feb. 18, 2020

(65) Prior Publication Data

US 2020/0264102 A1     Aug. 20, 2020

(30) Foreign Application Priority Data

Feb. 20, 2019   (JP) .............................. JP2019-028846

(51) Int. Cl.
*G01N 21/552*     (2014.01)
(52) U.S. Cl.
CPC .................................. *G01N 21/554* (2013.01)

(58) Field of Classification Search
CPC ...... G01N 21/55; G01N 21/553; G01N 21/41; G01N 21/783; G01N 21/658; G01N 33/005; G01N 23/553
USPC ..... 356/445–448, 432–440, 301; 422/88, 56, 422/57; 73/31.05, 23.2; 436/144, 147, 436/22
See application file for complete search history.

(56) References Cited

U.S. PATENT DOCUMENTS

| | | | | |
|---|---|---|---|---|
| 6,006,582 | A * | 12/1999 | Bhandari | G01N 21/783 257/2 |
| 8,675,200 | B2 * | 3/2014 | Suda | G01N 21/554 356/445 |
| 2005/0189223 | A1 * | 9/2005 | Yamaguchi | G01N 27/125 204/431 |
| 2012/0113424 | A1 | 5/2012 | Suda et al. | |
| 2012/0188551 | A1 * | 7/2012 | Langhammar | G01N 21/658 356/445 |

(Continued)

FOREIGN PATENT DOCUMENTS

| | | |
|---|---|---|
| JP | 2005-265590 | 9/2005 |
| WO | 2011/027899 | 3/2011 |

*Primary Examiner* — Hoa Q Pham
(74) *Attorney, Agent, or Firm* — Wenderoth, Lind & Ponack, L.L.P.

(57) ABSTRACT

A nanostructure array including a base body and a nanostructure formed on the base body, in which a plurality of the nanostructures are arranged on the nanostructure array, the nanostructure is made of a metal having a surface plasmon and a property of absorbing and releasing hydrogen, the base body is made of a hydrogen-responsive material that reacts with hydrogen to reversibly change from a conductor to a dielectric substance, and a surface plasmon resonance occurs by light incident on the nanostructure.

7 Claims, 3 Drawing Sheets

(56) References Cited

U.S. PATENT DOCUMENTS

| | | | |
|---|---|---|---|
| 2016/0103082 A1* | 4/2016 | Kimura | G01N 33/005 73/25.01 |
| 2016/0123878 A1* | 5/2016 | Zayats | G01N 33/005 356/445 |
| 2019/0310200 A1* | 10/2019 | Lee | G01N 21/65 |
| 2020/0088634 A1* | 3/2020 | Nishijima | G01N 21/553 |

* cited by examiner

NANOSTRUCTURE ARRAY, HYDROGEN DETECTION ELEMENT, AND HYDROGEN DETECTION DEVICE

BACKGROUND OF THE INVENTION

Field of the Invention

The present invention relates to a nanostructure array, a hydrogen detection element, and a hydrogen detection device.

Priority is claimed on Japanese Patent Application No. 2019-028846, filed on Feb. 20, 2019, the content of which is incorporated herein by reference.

Description of Related Art

In recent years, the use of hydrogen has attracted attention as the main energy for the next generation. On the other hand, hydrogen is a highly flammable gas, and prompt detection at the time of leakage is necessary for safe use.

In these circumstances, due to the safety concerns and low public awareness of hydrogen, development of a highly reliable hydrogen detection technique has been one of the most important issues in promoting the hydrogen-based industry.

As a conventional hydrogen detection means, a contact combustion system or a semiconductor system has been often used. In addition to these systems, a hydrogen detection system having a configuration in which the entire sensor unit is constituted of an optical system has been studied.

For example, Patent Literature 1 describes a technique of detecting hydrogen by detecting a change in light reflectance or transmittance associated with the hydrogenation using a hydrogen-sensitive dimming mirror.

Further, Patent Literature 2 describes a technique of detecting hydrogen by detecting a change in optical frequency characteristics associated with the hydrogen absorption using a surface plasmon resonance element configured by forming periodic openings in a thin film of palladium serving as a hydrogen-absorbing metal.

DOCUMENTS OF RELATED ART

Patent Literature

[Patent Literature 1] Japanese Unexamined Patent Application, First Publication No. 2005-265590
[Patent Literature 2] PCT International Publication No. WO2011/027899

SUMMARY OF THE INVENTION

However, in the above-described techniques of the related art, there is a problem in terms of the hydrogen response speed since absorption and release of hydrogen with respect to the hydrogen-absorbing metal takes time. In addition, the above-described techniques of the related art have further demands in terms of hydrogen detection sensitivity.

The present invention has been made in view of the above circumstances, and the object of the present invention is to provide a hydrogen detection element and a hydrogen detection device that quickly response to hydrogen and have increased hydrogen detection sensitivity, and a nanostructure array useful for them.

In order to achieve the above object, the present invention has employed the following configuration.

That is, a first aspect of the present invention is a nanostructure array including a base body and a nanostructure formed on the base body, in which a plurality of the nanostructures are arranged on the nanostructure array, the nanostructure is made of a metal having a surface plasmon and a property of absorbing and releasing hydrogen, the base body is made of a hydrogen-responsive material that reacts with hydrogen to reversibly change from a conductor to a dielectric substance, and a surface plasmon resonance occurs by light incident on the nanostructure.

A second aspect of the present invention is a hydrogen detection element detecting hydrogen based on a surface plasmon resonance, including the nanostructure array according to the first embodiment of the present invention on a base material.

A third aspect of the present invention is a hydrogen detection device, including the hydrogen detection element according to the second aspect of the present invention, a light source unit emitting light to the hydrogen detection element, a light receiving unit receiving the light through the hydrogen detection element, and a detection unit detecting hydrogen based on a light reception result of the light receiving unit.

According to the present invention, it is possible to provide a hydrogen detection element and a hydrogen detection device that quickly response to hydrogen and have increased hydrogen detection sensitivity, and a nanostructure array useful for them.

DETAILED DESCRIPTION OF THE INVENTION

A hydrogen detection device according to one aspect of the present invention is characterized by a hydrogen detection element, and various other known hydrogen detection devices can be appropriately applied to other configuration of the hydrogen detection device.

Figure 1:
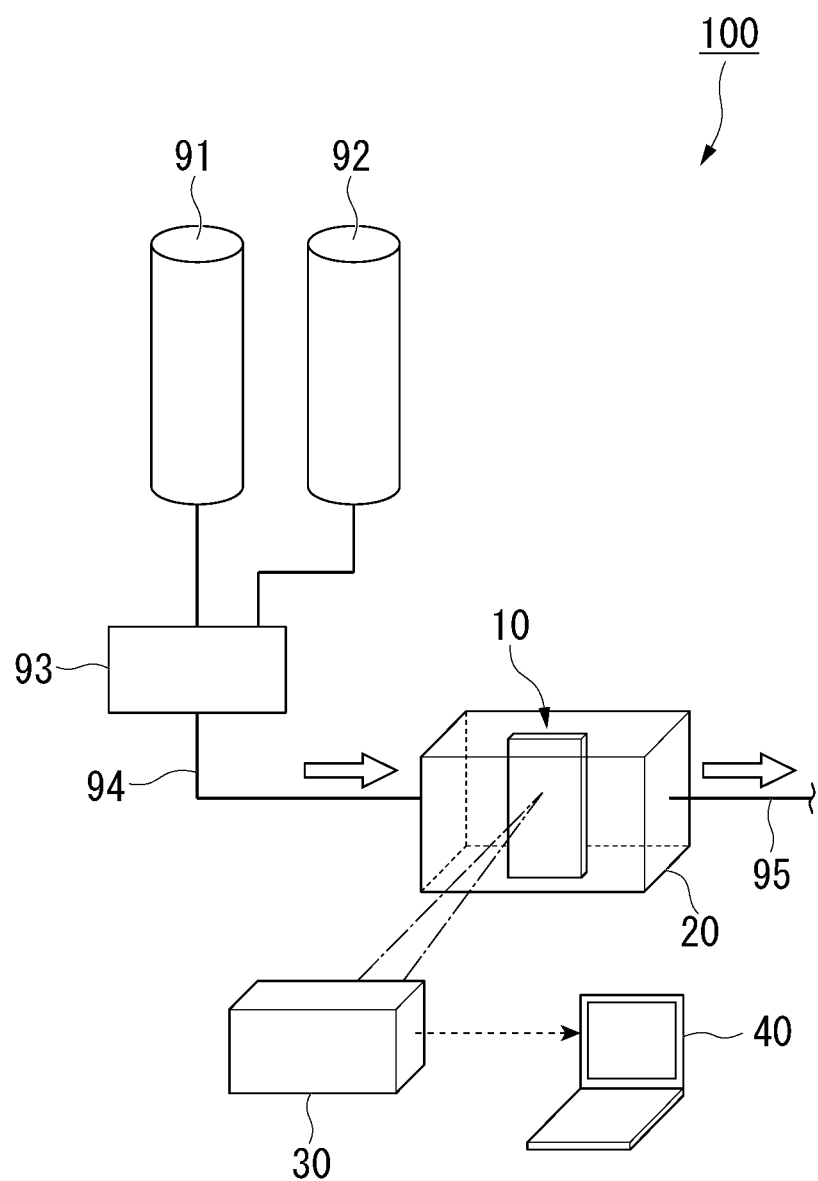
FIG. 1 is a diagram showing a schematic configuration of a hydrogen detection device according to the present embodiment.

FIG. 1 is a diagram showing a schematic configuration of a hydrogen detection device according to the present embodiment.

In FIG. 1, a hydrogen detection device 100 is a hydrogen sensor that detects hydrogen by using an optical technique and includes a hydrogen detection element 10, a light quantity measurement unit 30 having a light source unit and a light receiving unit, and a detection unit 40.

(Hydrogen Detection Element)

The hydrogen detection element 10 in the present embodiment includes a nanostructure array on a base material. In the hydrogen detection element 10, a surface plasmon resonance occurs by light incident on a nanostructure.

Figure 2:
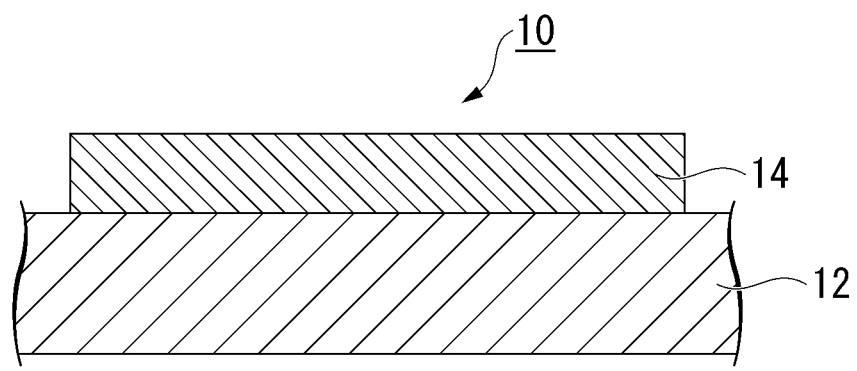
FIG. 2 is a partial cross-sectional view illustrating one embodiment of a hydrogen detection element.

FIG. 2 is a partial cross-sectional view illustrating one embodiment of a hydrogen detection element in a thickness direction.

In FIG. 2, the hydrogen detection element 10 includes a nanostructure array layer 14 on a base material layer 12.

The thickness of the base material layer 12 is, for example, 100 to 2,000

The thickness of the nanostructure array layer 14 is, for example, 300 to 500 nm.

Examples of the material for forming the base material layer 12 include a silicon wafer, a sapphire substrate, a silica glass substrate, a quartz glass substrate, a borosilicate glass substrate, an alumina substrate, an acrylic resin film, and a polyimide resin film.

Figure 3:
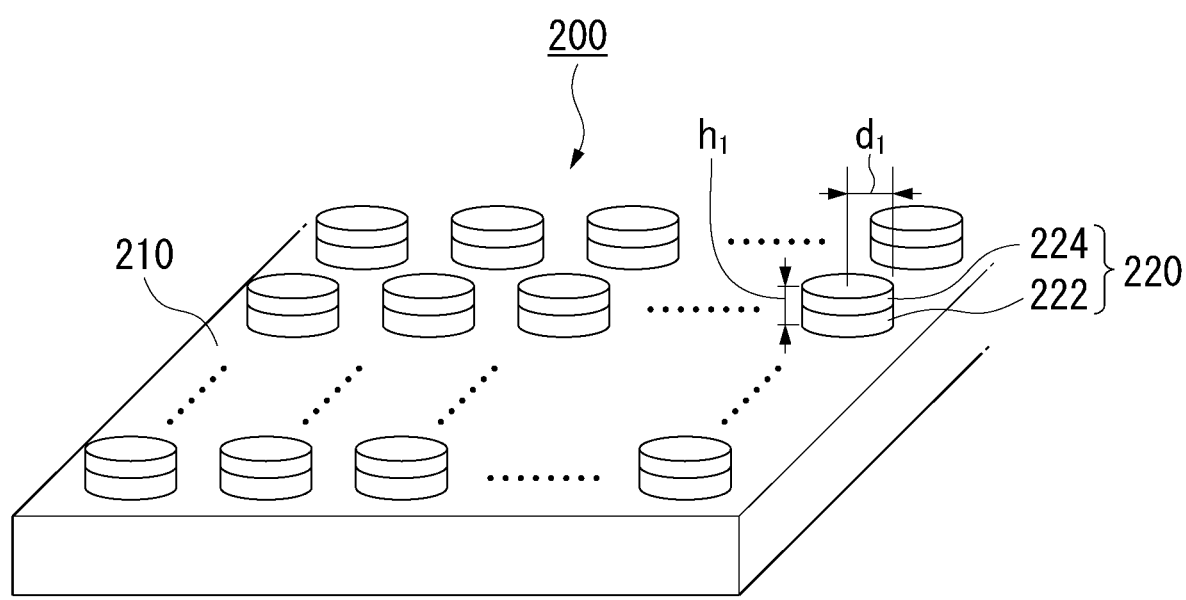
FIG. 3 is a perspective view illustrating one embodiment of a nanostructure array.
Figure 4:
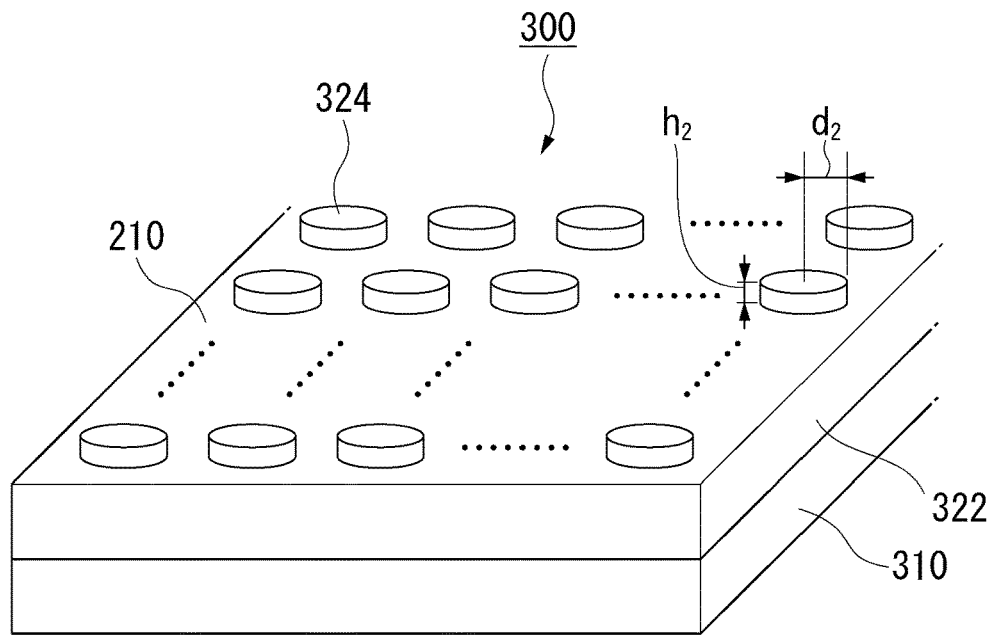
FIG. 4 is a perspective view illustrating other embodiment of the nanostructure array.

Examples of the nanostructure array layer 14 in the present embodiment include a layer formed of a nanostructure array shown in FIG. 3 (first embodiment) and a layer formed of a nanostructure array shown in FIG. 4 (second embodiment).

First Embodiment

FIG. 3 is a perspective view illustrating one embodiment of a nanostructure array.

In FIG. 3, a plurality of stacked bodies 220 are arranged two-dimensionally in a vertical and a horizontal direction on a metal layer 210 in a nanostructure array 200. The stacked body 220 is formed by stacking a base body 222 and a nanostructure 224.

In the nanostructure array 200, the metal layer 210 and the base body 222 are adjacent to each other, the base body 222 is disposed between the metal layer 210 and the nanostructure 224, and the nanostructure 224 is disposed on the outermost surface.

The stacked body 220 in the nanostructure array 200 has a substantially cylindrical shape, and its height ($h_1$) is, for example, preferably 100 to 300 nm in terms of hydrogen responsiveness and hydrogen detection sensitivity.

The radius ($d_1$) of the stacked body 220 is set according to the detection target (resonance wavelength), and is, for example, preferably 100 to 800 nm, and more preferably 400 to 800 nm.

The thickness of the base body 222 is, for example, 50 to 200 nm in terms of hydrogen responsiveness and hydrogen detection sensitivity.

The base body 222 is formed of a hydrogen-responsive material that reacts with hydrogen to reversibly change from a conductor to a dielectric substance and changes the behavior of a surface plasmon resonance of the nanostructure 224.

Examples of the material for forming the base body 222 include yttrium and lanthanoid elements (lanthanum, cerium, praseodymium, neodymium, promethium, samarium, eurobium, gadolinium, terbium, dysprosium, holmium, erbium, thulium, ytterbium, and lutetium). Among these, it is preferable to include at least one selected from the group consisting of yttrium and lanthanoid elements, and particularly preferable to include at least yttrium, in terms of hydrogen responsiveness and hydrogen detection sensitivity. Yttrium, which is a metal (Y) before hydrogen absorption, reversibly changes to an insulator ($YH_3$) after hydrogen absorption.

The thickness of the nanostructure 224 is, for example, 30 to 150 nm in terms of hydrogen responsiveness and hydrogen detection sensitivity.

The nanostructure 224 is formed of a metal having surface plasmons and having the property of absorbing and releasing hydrogen and is a material whose dielectric constant (refractive index) changes when hydrogen is absorbed.

Examples of materials forming the nanostructure 224 include transition metal elements from Group VII to Group XI of the periodic table (preferably transition metal elements of the fifth or sixth period from Group VII to Group X of the periodic table). Among these, palladium, noble metals other than palladium (gold, silver, platinum, rhodium, iridium, ruthenium, and osmium) are preferable. Among these, a metal including at least palladium is preferable in terms of hydrogen absorption and hydrogen release, and palladium alone or a combination of palladium and gold are particularly preferable.

The size of the metal layer 210 can be appropriately determined according to the usage applications.

The thickness of the metal layer 210 is, for example, 100 to 500 nm in terms of strength, hydrogen responsiveness and hydrogen detection sensitivity.

Examples of the material for forming the metal layer 210 include transition metal elements from Group VII to Group XI the periodic table such as gold, silver, copper, palladium, platinum, rhodium, and osmium (preferably transition metal elements of the fifth or sixth period from Group VII to Group X of the periodic table), aluminum, cesium and alloys selected from these elements. Among these, it is preferable to include at least one selected from the group consisting of gold, silver, copper, palladium, and platinum in terms of hydrogen responsiveness and hydrogen detection sensitivity, more preferable to include at least one selected from the group consisting of gold and palladium, and particularly preferable to include at least gold.

In FIG. 3, a plurality of stacked bodies 220 are arranged on the metal layer 210 at a predetermined cycle (pitch). The distance (cycle) between the stacked bodies 220 is preferably larger than a diameter ($2d_1$) in terms of hydrogen responsiveness and hydrogen detection sensitivity and is more preferably 1.1 to 2 times the diameter ($2d_1$).

The hydrogen detection element including a layer formed of the nanostructure array 200 of the first embodiment on the base material layer 12 can be manufactured, for example, according to following Procedures (A1) to (A4).

Procedure (A1): The metal layer 210 is formed on the base material layer 12 by using a thermal evaporation method.

Procedure (A2): A positive photoresist is applied on the metal layer 210 by spin coating or the like to form a photoresist film. Thereafter, the photoresist film is exposed through a mask having opening portions corresponding to the arrangement and diameter of the plurality of stacked bodies 220. Then, the photoresist film in a region where the plurality of stacked bodies 220 are formed is removed by development, and a photoresist pattern is formed on the metal layer 210.

Procedure (A3): A layer containing a material forming the base body 222 and a layer containing a material forming the nanostructure 224 are stacked in this order on the metal layer 210 on which the photoresist pattern is formed by sputtering or the like.

Procedure (A4): Using an organic solvent or the like, the photoresist pattern formed on the metal layer 210 and the two layers stacked on the photoresist pattern are removed (that is, by a lift-off method).

In addition, the hydrogen detection element including a layer formed of the nanostructure array 200 of the first embodiment on the base material layer 12 can be also manufactured, for example, according to following Procedures (B1) to (B4).

Procedure (B1): The metal layer 210 is formed on the base material layer 12 by using a thermal evaporation method.

Procedure (B2): A layer containing a material forming the base body 222 and a layer containing a material forming the nanostructure 224 are stacked in this order on the metal layer 210 by sputtering or the like.

Procedure (B3): A negative photoresist is applied on the layer containing a material forming the nanostructure 224 by spin coating or the like to form a photoresist film. Thereafter, the photoresist film is exposed through a mask having opening portions corresponding to the arrangement and diameter of the plurality of stacked bodies 220. Then, the photoresist film outside a region where the plurality of stacked bodies 220 are formed is removed by development, and a photoresist pattern is formed on a layer containing a material forming the nanostructure 224.

Procedure (B4): The two layers stacked on the metal layer 210 in the region outside the photoresist pattern are removed by etching.

As described above, the hydrogen detection element 10 of the present embodiment quickly response to hydrogen and have increased hydrogen detection sensitivity, since the specific nanostructure array 200 are provided.

In the nanostructure array 200, the base body 222 before hydrogen absorption is a conductor (metal), and the base body 222 after hydrogen absorption reversibly changes to an insulator. With this change, since the behavior of surface plasmon resonance changes before and after hydrogen absorption, the optical characteristics change. That is, in the hydrogen detection device 100, the hydrogen detection sensitivity increases and the amount of change in reflectance increases.

In the nanostructure array 200 of the first embodiment described above, the stacked body 220 in which the base body 222 and the nanostructure 224 are stacked has a cylindrical shape, but the present invention is not limited thereto, and the stacked body 220 may have, for example, a square-pillar or triangle-pillar shape.

In addition, although in the stacked body 220 of the first embodiment, the base body 222 has the same diameter as the diameter of the nanostructure 224, but not limited thereto, and both shape and dimension therebetween may be different.

In the nanostructure array 200 of the first embodiment, the plurality of stacked bodies 220 are two-dimensionally arranged on the metal layer 210 in a vertical and a horizontal direction at a predetermined cycle (pitch), but the arrangement is not limited thereto. The arrangement of the plurality of stacked bodies 220 can be appropriately set according to the purpose or the like.

Second Embodiment

FIG. 4 is a perspective view illustrating other embodiment of the nanostructure array.

In FIG. 4, a plurality of nanostructures 324 are arranged two-dimensionally in a vertical and a horizontal direction on a base body layer 322 adjacent to a metal layer 310 in a nanostructure array 300.

In the nanostructure array 300, the metal layer 310 and the base body layer 322 are adjacent to each other, the base body layer 322 is disposed between the metal layer 310 and the nanostructure 324, and the nanostructure 324 is disposed on the outermost surface.

The thickness of the base body layer 322 is, for example, 50 to 200 nm in terms of hydrogen responsiveness and hydrogen detection sensitivity.

The base body layer 322 is formed of a hydrogen-responsive material that reacts with hydrogen to reversibly change from a conductor to a dielectric substance and changes the behavior of a surface plasmon resonance of the nanostructure 324.

Examples of materials forming the base body layer 322 include metal trioxides, metal pentoxides, and alloys containing magnesium.

Examples of the metal trioxides include $WO_3$, $MoO_3$, and $ReO_3$.

Examples of the metal pentoxides include $V_2O_5$, $Nb_2O_5$, and $Ta_2O_5$.

Examples of the alloys containing magnesium include MgTi, NiMg, ErMg, GdMg, and SmMg.

Among these, the material forming the base body layer 322 preferably includes at least one selected from the group consisting of metal trioxides, metal pentoxides, and alloys containing magnesium in terms of hydrogen responsiveness and hydrogen detection sensitivity, more preferably at least metal trioxides, and particularly preferably at least $WO_3$. Tungsten oxide, which is an insulator before hydrogen absorption ($WO_3$), reversibly changes to a metal-like compound (conductor) after hydrogen absorption ($H_xWO_3$).

The nanostructure 324 in the nanostructure array 300 has a substantially cylindrical shape, and its height ($h_2$) is, for example, preferably 50 to 150 nm in terms of hydrogen responsiveness and hydrogen detection sensitivity.

The radius ($d_2$) of the nanostructure 324 is set according to the detection target (resonance wavelength), and is, for example, preferably 100 to 800 nm, and more preferably 400 to 800 nm.

The nanostructure 324 is formed of a metal having surface plasmons and having the property of absorbing and releasing hydrogen and is a material whose dielectric constant (refractive index) changes when hydrogen is absorbed.

Examples of materials forming the nanostructure 324 include transition metal elements from Group VII to Group XI of the periodic table (preferably transition metal elements of the fifth or sixth period from Group VII to Group X of the periodic table). Among these, palladium, noble metals other than palladium (gold, silver, platinum, rhodium, iridium, ruthenium, and osmium) are preferable. Among these, a metal including at least palladium is preferable in terms of hydrogen absorption and hydrogen release, and palladium alone or a combination of palladium and gold are particularly preferable.

The size of the metal layer 310 can be appropriately determined according to the usage applications.

The thickness of the metal layer 310 is, for example, 100 to 500 nm in terms of strength, hydrogen responsiveness and hydrogen detection sensitivity.

Examples of the material for forming the metal layer 310 include transition metal elements from Group VII to Group XI the periodic table such as gold, silver, copper, palladium, platinum, rhodium, and osmium (preferably transition metal elements of the fifth or sixth period from Group VII to Group X of the periodic table), aluminum, cesium and alloys selected from these elements. Among these, it is preferable to include at least one selected from the group consisting of gold, silver, copper, palladium, and platinum in terms of hydrogen responsiveness and hydrogen detection sensitivity, more preferable to include at least one selected from the group consisting of gold and palladium, and particularly preferable to include at least gold.

In FIG. 4, a plurality of nanostructures 324 are arranged on the base body layer 322 at a predetermined cycle (pitch). The distance (cycle) between the nanostructures 324 is preferably larger than a diameter ($2d_2$) in terms of hydrogen responsiveness and hydrogen detection sensitivity and is more preferably 1.1 to 2 times the diameter ($2d_2$).

The hydrogen detection element including a layer formed of the nanostructure array 300 of the second embodiment on the base material layer 12 can be manufactured, for example, according to following Procedures (C1) to (C5).

Procedure (C1): The metal layer 310 is formed on the base material layer 12 by using a thermal evaporation method.

Procedure (C2): The base body layer 322 is formed on the metal layer 310 by sputtering or the like.

Procedure (C3): A positive photoresist is applied on the base body layer 322 by spin coating or the like to form a photoresist film. Thereafter, the photoresist film is exposed through a mask having opening portions corresponding to the arrangement and diameter of the plurality of nanostructures 324. Then, the photoresist film in a region where the plurality of nanostructures 324 are formed is removed by development, and a photoresist pattern is formed on the base body layer 322.

Procedure (C4): A layer containing a material forming the nanostructure 324 is stacked on the base body layer 322 on which the photoresist pattern is formed by sputtering or the like.

Procedure (C5): Using an organic solvent or the like, the photoresist pattern formed on the base body layer 322 and the layer stacked on the photoresist pattern are removed (that is, by a lift-off method).

In addition, the hydrogen detection element including a layer formed of the nanostructure array 300 of the second embodiment on the base material layer 12 can be also manufactured, for example, according to following Procedures (D1) to (D4).

Procedure (D1): The metal layer 310 is formed on the base material layer 12 by using a thermal evaporation method.

Procedure (D2): The base body layer 322 and a layer containing a material forming the nanostructure 324 are stacked in this order on the metal layer 310 by sputtering or the like.

Procedure (D3): A negative photoresist is applied on the layer containing a material forming the nanostructure 324 by spin coating or the like to form a photoresist film. Thereafter, the photoresist film is exposed through a mask having opening portions corresponding to the arrangement and diameter of the plurality of nanostructures 324. Then, the photoresist film outside a region where the plurality of nanostructures 324 are formed is removed by development, and a photoresist pattern is formed on a layer containing a material forming the nanostructure 324.

Procedure (D4): The layer in the region outside the photoresist pattern, containing a material forming the nanostructure 324 and stacked on the base body layer 322, is removed by etching.

As described above, the hydrogen detection element 10 of the present embodiment quickly response to hydrogen and have increased hydrogen detection sensitivity, since a specific nanostructure array 300 is provided.

In the nanostructure array 300, the base body layer 322 before hydrogen absorption is an insulator, and the base body layer 322 after hydrogen absorption reversibly changes to a metal-like compound. With this change, since the behavior of surface plasmon resonance changes before and after hydrogen absorption, the optical characteristics change. That is, in the hydrogen detection device 100, the hydrogen detection sensitivity increases and the amount of change in reflectance increases.

In the nanostructure array 300 of the second embodiment described above, the nanostructure 324 has a cylindrical shape, but the present invention is not limited thereto, and the nanostructure 324 may have, for example, a square-pillar or triangle-pillar shape.

In the nanostructure array 300 of the second embodiment, the plurality of nanostructures 324 are two-dimensionally arranged on the base body layer 322 in a vertical and a horizontal direction at a predetermined cycle (pitch), but the arrangement is not limited thereto. The arrangement of the plurality of nanostructures 324 can be appropriately set according to the purpose or the like.

Other Embodiments

In the hydrogen detection element 10 of the first embodiment described above, the plurality of stacked bodies 220 (in which the base body 222 and the nanostructure 224 are stacked) are arranged on the metal layer 210. However, the present invention is not limited thereto. As in the second embodiment, a configuration in which the plurality of nanostructures 224 are two-dimensionally arranged in a vertical and a horizontal direction on the base body layer (the layer formed of the base body 222) adjacent to the metal layer 210 may be adopted. However, a plurality of materials forming the base body 222, such as yttrium Y, have high oxidation property. For this reason, it is preferable to coat the exposed portion of the base body layer (the layer formed of the base body 222) with an antioxidant film.

Each of the hydrogen detection elements 10 of the first embodiment and the second embodiment described has a configuration including the metal layers 210 and 310, but the configuration is not limited thereto, and a configuration which lacks the metal layers 210 and 310 may be adopted.

That is, a hydrogen detection element (third embodiment) may have a configuration in which a plurality of stacked bodies of a base body and a nanostructure are arranged on a base material layer may be adopted, or a hydrogen detection element (fourth embodiment) may have a configuration in which a plurality of nanostructures are arranged on a base body layer adjacent to a base material layer may be adopted.

In a hydrogen detection device to which the hydrogen detection element of the third embodiment or the fourth embodiment is applied, a configuration in which infrared light transmitted through the hydrogen detection element is received or a configuration in which infrared light reflected by the hydrogen detection element is received can be adopted.

In addition, according to the third embodiment or the fourth embodiment, a hydrogen detection element with a metal hole array type or with a nanodisk array type can be employed.

(Hydrogen Detection Device)

A hydrogen detection device according to one embodiment of the present invention includes a hydrogen detection element, a light source unit emitting light to the hydrogen detection element, a light receiving unit receiving light through the hydrogen detection element, and a detection unit detecting hydrogen based on a light reception result of the light receiving unit.

In FIG. 1, a hydrogen detection device 100 includes a hydrogen detection element 10, a light quantity measurement unit 30 having a light source unit and a light receiving unit, and a detection unit 40.

In the hydrogen detection device 100 of the present embodiment, the hydrogen detection element 10 is one to which the present invention is applied (one including a nanostructure array layer 14 on a base material layer 12). As the nanostructure array layer 14, the nanostructure array of the first embodiment or the second embodiment described above can be employed.

The hydrogen detection element 10 is accommodated in a chamber 20.

The pipe 94 to which a mixed gas including hydrogen is introduced and a pipe 95 from which the mixed gas is discharged are connected to a chamber 20. In addition, a mixer 93 is connected to the chamber 20 through the pipe 94.

In the mixer 93, the nitrogen supplied from a nitrogen supply unit 91 and the hydrogen-including gas supplied from a hydrogen supply unit 92 are mixed at a predetermined mixing ratio.

The hydrogen detection device 100 of the present embodiment can detect hydrogen in a case where the concentration of hydrogen included in the mixed gas is, for example, 4% by volume or more, can sufficiently detect hydrogen of 1% by volume or more, and can even detect hydrogen of 0.01% by volume or more by suitably selecting a nanostructure array or the like.

The flow rate of the mixed gas from the mixer 93 to the chamber 20 may be suitably set according to the device scale or the like, for example, in a case where the capacity of the chamber 20 is 1.5 L, the flow rate of the mixed gas is preferably set to 1,500 mL/h or more, and it is preferable that the flow rate per unit time is large.

In the hydrogen detection device 100 of the present embodiment, the light quantity measurement unit 30 has both a light source unit and a light receiving unit. The light quantity measurement unit 30 emits, as a light source unit, light having a predetermined wavelength to the hydrogen detection element 10 in the chamber 20. The light emitted from the light source unit can be suitably selected according to the size of the nanostructure, include, for example, infrared light, and preferably include near-infrared to mid-infrared rays.

The light quantity measurement unit 30 receives, as a light receiving unit, light reflected by the hydrogen detection element 10. Further, the light quantity measurement unit 30 outputs information received by the light receiving unit to the detection unit 40.

For the light quantity measurement unit 30, for example, a spectrophotometer such as a Fourier transform infrared spectrophotometer (FT-IR) can be used.

The detection unit 40 detects hydrogen by performing a calculation from a light reception result of the light receiving unit in the light quantity measurement unit 30 based on a surface plasmon resonance. Specifically, the detection unit 40 detects hydrogen according to a difference between the reflectance of infrared light before hydrogen absorption in the hydrogen detection element 10 and the reflectance of infrared light after hydrogen absorption in the hydrogen detection element 10 based on the information received.

In the hydrogen detection device 100 of the present embodiment, the hydrogen detection element 10 is irradiated with light (for example, infrared light with a wavelength of 1,300 nm) emitted from the light source unit in the light quantity measurement unit 30, and a part of the infrared light is reflected by the hydrogen detection element 10 and is incident on the light receiving unit in the light quantity measurement unit 30.

The mixed gas including hydrogen is supplied from the mixer 93 to the chamber 20. In the hydrogen detection element 10 accommodated in the chamber 20, a surface plasmon resonance occurs by light incident on a nanostructure. In addition, a metal constituting the nanostructure array absorbs hydrogen. Hydrogen absorbed in the metal is purified in the metal, diffuses into the base body, and reacts with a hydrogen-responsive material. With this change, since the behavior of the surface plasmon resonance changes before and after hydrogen absorption, the optical characteristics change. In the hydrogen detection device 100, a reflection spectrum shifts to a short wavelength side or a long wavelength side. In this way, hydrogen included in the mixed gas is detected, and the hydrogen detection device 100 functions as a hydrogen sensor.

In addition, in the hydrogen detection device 100 of the present embodiment, it is preferable to use a hydrogen detection element exposed to hydrogen in advance before using for hydrogen detection.

For example, in a case where the hydrogen detection element of the first embodiment or the second embodiment described above is applied as the hydrogen detection element 10, the hydrogen detection element to be used is exposed to hydrogen before used for hydrogen detection, preferably in advance for 0.5 hour or more to 2 days and more preferably in advance for 1 hour or more to 1 day. By using the hydrogen detection element which has been exposed to hydrogen in advance in the above preferred time range, response to hydrogen can be accelerated, and hydrogen detection sensitivity can be increased.

In a case where a hydrogen detection element which has been exposed to hydrogen in advance is used, in the hydrogen detection device 100 to which the hydrogen detection element of the first embodiment is applied, a reflection spectrum shifts to the short wavelength side. In the hydrogen detection device 100 to which the hydrogen detection element of the second embodiment is applied, a reflection spectrum shifts to the long wavelength side. That is, the hydrogen detection device 100 is excellent in hydrogen responsiveness and hydrogen detection sensitivity.

The nanostructure arrays 200 and 300 of the present embodiment quickly response to hydrogen and have increased hydrogen detection sensitivity, since the nanostructures 224 and 324 are formed on the base bodies 222 and 322, respectively. In addition, the nanostructure arrays 200 and 300 have particularly enhanced hydrogen detection sensitivity, since the metal layers 210 and 310 are provided respectively.

In the hydrogen detection device 100 of the embodiment described above, the configuration in which the light reflected by the hydrogen detection element 10 is received is employed. However, the configuration is not limited thereto, and, for example, a device configured to receive light transmitted through the hydrogen detection element 10 or diffracted light may be employed.

EXAMPLE

Hereinafter, the present invention will be further described in detail according to Examples, but the present invention is not limited by these examples.

<Manufacture of Hydrogen Detection Element>

A hydrogen detection element of the same embodiment as the embodiment for the hydrogen detection element 10 shown in FIG. 2, that is, a hydrogen detection element including a nanostructure array layer on a base material layer was manufactured as follows.

The hydrogen detection elements of Examples 1, 2, and 5 to 12 included the same nanostructure array layer as that of the first embodiment shown in FIG. 3.

The hydrogen detection elements of Examples 3, 4, and 13 to 20 included the same nanostructure array layer as that of the second embodiment shown in FIG. 4.

Example 1

Procedure (a1): A chromium (Cr) layer having a thickness of 3 nm and a gold (Au) layer having a thickness of 200 nm were deposited in this order on a glass substrate by a thermal vapor deposition method.

Procedure (a2): A photoresist pattern (having a pattern of 400 nm of radius hole and a cycle of 1.5 times the diameter) was formed on the gold (Au) layer by an electron beam lithography.

Procedure (a3): An yttrium (Y) layer having a thickness of 100 nm and a palladium (Pd) layer having a thickness of 50 nm were deposited in this order on the gold (Au) layer on which the photoresist pattern was formed, by using an electron beam vapor deposition method.

Procedure (a4): The photoresist pattern formed on the gold (Au) layer and the two layers (yttrium (Y) layer and palladium (Pd) layer) stacked on the photoresist pattern were removed by a lift-off method.

As a result, a hydrogen detection element was obtained, which included a nanodisk array layer in which disk-shaped stacked bodies (Y layer and Pd layer) having a radius of 400 nm were two-dimensionally arranged in a vertical and a horizontal direction (cycle: 1.5 times the diameter) on the gold (Au) layer.

Example 2

Procedures (a1) to (a4) were carried out in the same manner as in Example 1. Thereafter, exposure to pure hydrogen was performed for 1 hour, and a hydrogen detection element of Example 2 was obtained, which included a nanodisk array layer in which disk-shaped stacked bodies (Y layer and Pd layer) having a radius of 400 nm were two-dimensionally arranged in a vertical and a horizontal directions (cycle: 1.5 times the diameter) on the gold (Au) layer.

Example 3

Procedure (c1): A chromium (Cr) layer having a thickness of 3 nm and a gold (Au) layer having a thickness of 200 nm were deposited in this order on a glass substrate by a thermal vapor deposition method.

Procedure (c2): A tungsten oxide ($WO_3$) layer having a thickness of 100 nm was deposited on the gold (Au) layer by using the electron beam vapor deposition method.

Procedure (c3): A photoresist pattern (having a pattern of 400 nm of radius hole and a cycle of 1.5 times the diameter) was formed on the tungsten oxide ($WO_3$) layer by the electron beam lithography.

Procedure (c4): A palladium (Pd) layer having a thickness of 50 nm was deposited on the tungsten oxide ($WO_3$) layer on which the photoresist pattern was formed by using the electron beam vapor deposition method.

Procedure (c5): The photoresist pattern formed on the tungsten oxide ($WO_3$) layer and the palladium (Pd) layer stacked on the photoresist pattern were removed by the lift-off method.

As a result, a hydrogen detection element was obtained, which included a nanodisk array layer in which disk-shaped palladium (Pd) nanostructures having a radius of 400 nm were two-dimensionally arranged in a vertical and a horizontal direction (cycle: 1.5 times the diameter) on the $WO_3$ layer adjacent to the gold (Au) layer.

Example 4

Procedures (c1) to (c5) were carried out in the same manner as in Example 3. Thereafter, exposure to pure hydrogen was performed for 1 hour, and a hydrogen detection element of Example 4 was obtained, which included a nanodisk array layer in which disk-shaped palladium (Pd) nanostructures having a radius of 400 nm were two-dimensionally arranged in a vertical and a horizontal directions (cycle: 1.5 times the diameter) on the $WO_3$ layer adjacent to the gold (Au) layer.

Examples 5 to 12

Procedures (a1) to (a4) and exposure to pure hydrogen for 1 hour were performed in the same manner as in Example 2 except that the hole radius was respectively changed to 450 nm, 500 nm, 550 nm, 600 nm, 650 nm, 700 nm, 750 nm, and 800 nm in above Procedure (a2), and each hydrogen detection element of Examples 5 to 12 was obtained.

Examples 13 to 20

Procedures (c1) to (c5) and exposure to pure hydrogen for 1 hour were performed in the same manner as in Example 4 except that the hole radius was respectively changed to 450 nm, 500 nm, 550 nm, 600 nm, 650 nm, 700 nm, 750 nm, and 800 nm in above Procedure (c3), and each hydrogen detection element of Examples 13 to 20 was obtained.

Comparative Example 1

A chromium (Cr) layer having a thickness of 3 nm and a gold (Au) layer having a thickness of 200 nm were deposited in this order on a glass substrate by the thermal vapor deposition method. Next, a yttrium (Y) layer having a thickness of 100 nm and a palladium (Pd) layer having a thickness of 50 nm were deposited in this order on the entire surface of a gold (Au) layer, by using the electron beam vapor deposition method. Then, exposure to pure hydrogen was performed for 4 seconds, and a hydrogen detection element of Comparative Example 1 which included a stacked body of an Au layer/an Y layer/a Pd layer, was obtained.

<Evaluation>

A device of the same embodiment as the embodiment for the hydrogen detection device 100 shown in FIG. 1 was manufactured, and a mixed gas was supplied into the chamber, and a reflection spectrum was measured.

For the hydrogen detection element 10, the hydrogen detection elements of Examples 1 to 20 and Comparative Example 1 were applied. For the light quantity measurement unit 30 having the light source unit and the light receiving unit, a Fourier transform infrared spectrophotometer (FT-IR) was used.

[Measurement Condition]

Light emitted from the light source unit in the light quantity measurement unit 30: infrared light having a wavelength of 1,300 nm Ratio of gas mixture: nitrogen/hydrogen=96/4 (volume ratio)

Figure 5:
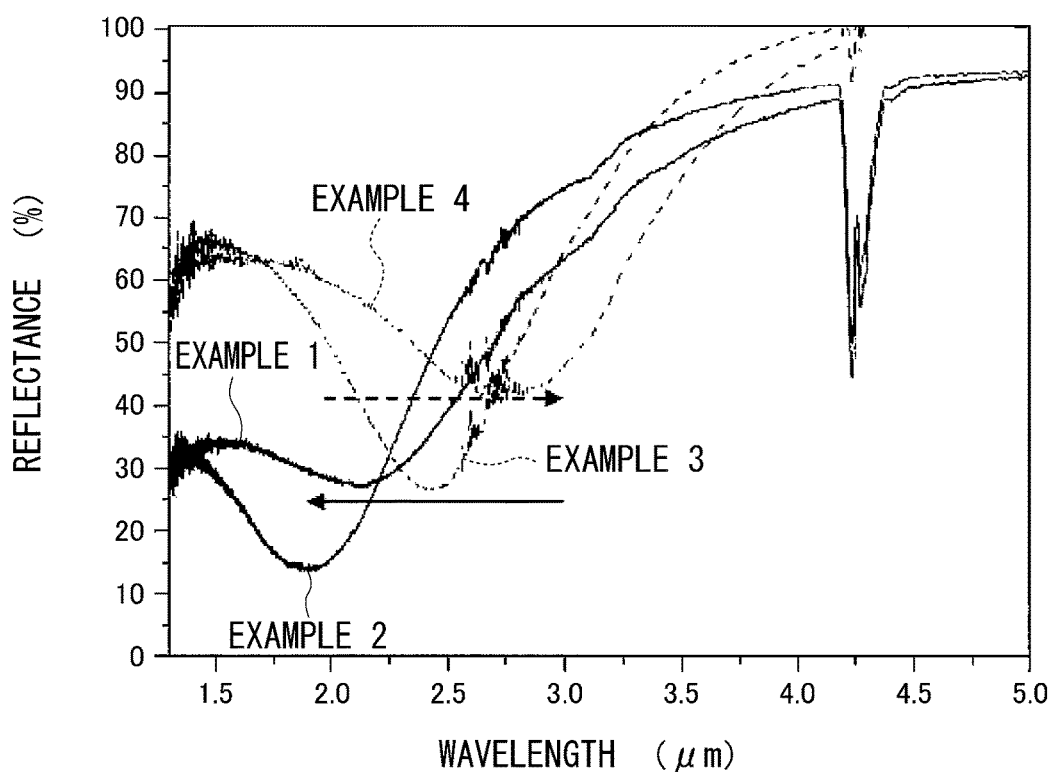
FIG. 5 is a graph showing the relationship (reflection spectrum) of an infrared light wavelength and a reflectance, which is obtained by measurement with a Fourier transform infrared spectrophotometer (FT-IR) applied to the hydrogen detection device to which each of the hydrogen detection elements of Examples 1 and 2 and Examples 3 and 4 is applied.

The flow rate of the mixed gas supplied from the mixer 93 to the chamber 20: 1,500 mL/h FIG. 5 is a graph showing the relationship (reflection spectrum) of an infrared light wavelength and a reflectance, which is obtained by measurement with a Fourier transform infrared spectrophotometer (FT-IR). The horizontal axis indicates the wavelength (m), and the vertical axis indicates the reflectance (%).

FIG. 5 is a graph showing the relationship (reflection spectrum) of an infrared light wavelength and a reflectance, which is obtained by measurement with a Fourier transform infrared spectrophotometer (FT-IR) applied to the hydrogen detection device to which each of the hydrogen detection elements of Examples 1 and 2 and Examples 3 and 4 is applied.

In a case where the hydrogen detection element of Comparative Example 1 was applied, the hydrogen response speed was about the same as in the case where the hydrogen detection element of Example 2 was applied. On the other hand, in the case where the hydrogen detection element of Comparative Example 1 was applied, the change in the reflectance was very small, and the hydrogen detection sensitivity was very weak.

It was confirmed that the hydrogen detection element of Comparative Example 1, which includes a stacked body of Au layer/Y layer/Pd layer, reacts with hydrogen within 4 seconds after starting exposure to pure hydrogen (hydrogen absorption) and releases hydrogen at 4 seconds after stopping exposure to pure hydrogen.

In FIG. 5, in a case where the hydrogen detection element of Example 2 was applied, a dip with an extremely low reflectance at a specific wavelength was observed. From this, it can be confirmed that the hydrogen detection sensitivity is further enhanced by providing the nanostructure array.

Comparison in a case where each of the hydrogen detection elements of Example 1 and Example 2 was applied:

It was observed that a reflection spectrum in a case where the hydrogen detection element of Example 2 was applied was shifted to a short wavelength side (blue shift) in comparison with a reflection spectrum in a case where the hydrogen detection element of Example 1 was applied, and the dip with the extremely low reflectance at the specific wavelength was more remarkable (the transmittance is increased). From this, it can be confirmed that by performing exposure to pure hydrogen for 1 hour in advance before a hydrogen detection test, the response to hydrogen can be accelerated and the hydrogen detection sensitivity can be increased.

It is speculated that since yttrium (Y) changes from Y to $YH_2$ by performing exposure to pure hydrogen for 1 hour and a surface plasmon resonance occurs easily, the reflection spectrum shift of the hydrogen detection element of Example 2 is obtained.

Comparison in a case where each of the hydrogen detection elements of Example 3 and Example 4 was applied:

It was observed that a reflection spectrum in a case where the hydrogen detection element of Example 4 was applied was shifted to a long wavelength side (red shift) in comparison with a reflection spectrum in a case where the hydrogen detection element of Example 3 was applied and the reflectance was increased. From this, it can be confirmed that by performing exposure to pure hydrogen for 1 hour in advance before a hydrogen detection test, the response to hydrogen can be accelerated and the hydrogen detection sensitivity can be increased.

It is speculated that since tungsten oxide ($WO_3$) changes from $WO_3$ to $H_xWO_3$ by performing exposure to pure hydrogen for 1 hour and the surface plasmon resonance disappears easily, the reflection spectrum shift of the hydrogen detection element of Example 4 is obtained.

In any cases where the hydrogen detection elements of Examples 5 to 12 were applied, reflection spectra showing changes similar to the reflection spectrum measured in the case where the hydrogen detection element of Example 2 was applied were obtained. However, as the disk radius increased, the reflection spectrum shifted to a long wavelength side.

In any cases where the hydrogen detection elements of Examples 13 to 20 were applied, reflection spectra showing changes similar to the reflection spectrum measured in the case where the hydrogen detection element of Example 4 was applied were obtained. However, as the disk radius increased, the reflection spectrum shifted to a long wavelength side.

From the above results, it was proved that the hydrogen detection device employing the hydrogen detection element to which the hydrogen detection elements of Examples 1, 2, and 5 to 12 are applied operate as a hydrogen sensor.

In addition, it was proved that the hydrogen detection device employing the hydrogen detection element to which the hydrogen detection elements of Examples 3, 4, and 13 to 20 are applied operate as a hydrogen sensor.

The hydrogen detection element and the hydrogen detection device according to the present invention can be used in various applications using hydrogen as a fuel for detection of hydrogen leakage or the like. The hydrogen detection element and the hydrogen detection device according to the present invention can be installed in, for example, a fuel cell, a vehicle using hydrogen as an energy source, a gas turbine using hydrogen as an energy source, and the like.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description and is only limited by the scope of the appended claims.

EXPLANATION OF REFERENCES

10 Hydrogen detection element
12 Base material layer
14 Nanostructure array layer
30 Light quantity measurement unit
40 Detection unit
100 Hydrogen detection device
200 Nanostructure array
210 Metal layer
220 Stacked body
222 Base body
224 Nanostructure
300 Nanostructure array
310 Metal layer
322 Base body layer
324 Nanostructure

What is claimed is:

1. A nanostructure array comprising:
a metal layer including at least one selected from a group consisting of gold, silver, copper, palladium and platinum, the metal layer being in the form of a generally flat sheet having a thickness of 100 to 500 nm; and
a plurality of stacked bodies formed on the metal layer and arranged in an array, each of the stacked bodies consisting of:
a base body being made of a hydrogen-responsive material that reacts with hydrogen to reversibly change from a conductor to a dielectric substance, deposited on the metal layer, the hydrogen-responsive material being at least one selected from a group consisting of yttrium and lanthanoid elements; and
a nanostructure being made of a metal having a surface plasmon and a property of absorbing and releasing hydrogen, and formed on the base body,
wherein each of the plurality of the stacked bodies is in a disc shape, and
the plurality of the stacked bodies are structurally independent from each other.

2. The nanostructure array according to claim 1, wherein the nanostructure is made of a metal comprising at least palladium.

3. A hydrogen detection element for detecting hydrogen based on a surface plasmon resonance, the hydrogen detection element comprising:
the nanostructure array according to claim 1 on a base material.

4. A hydrogen detection device comprising:
the hydrogen detection element according to claim 3;
a light source unit emitting light to the hydrogen detection element;
a light receiving unit receiving the light through the hydrogen detection element; and
a detection unit detecting hydrogen based on a light reception result of the light receiving unit.

5. The nanostructure array according to claim 1, wherein the distance between adjacent stacked bodies is 1.1 to 2 times a diameter ($2d_1$) of a stacked body.

6. A nanostructure array comprising:
a metal layer including at least one selected from a group consisting of gold, silver, copper, palladium and platinum, the metal layer being in the form of a generally flat sheet having a thickness of 100 to 500 nm; and
a plurality of stacked bodies formed on the metal layer and arranged in an array, each of the stacked bodies consisting of:
a base body being made of a hydrogen-responsive material that reacts with hydrogen to reversibly change from a conductor to a dielectric substance, and deposited on the metal layer; and
a nanostructure being made of a metal having a surface plasmon and a property of absorbing and releasing hydrogen, and formed on the base body,
wherein the hydrogen-responsive material comprises at least one selected from the group consisting of $WO_3$, $MoO_3$, $ReO_3$, $V_2O_5$, $Nb_2O_5$, $Ta_2O_5$, and a magnesium alloy consisting of metals,
each of the plurality of the stacked bodies is in a disc shape, and
the plurality of the stacked bodies are structurally independent from each other.

7. The nanostructure array according to claim 6, wherein the hydrogen-responsive material comprises at least one selected from the group consisting of MgTi, NiMg, ErMg, GdMg, and SmMg.

* * * * *